United States Patent [19]

Castaldi et al.

[11] Patent Number: 4,550,191
[45] Date of Patent: Oct. 29, 1985

[54] PROCESS FOR PREPARING ESTERS OF 2'-(6'-METHOXY-2-NAPHTHYL)-PROPIONIC ACID

[75] Inventors: Graziano Castaldi, Briona; Claudio Giordano, Vicenza, both of Italy

[73] Assignee: Blaschim S.p.A., Milan, Italy

[21] Appl. No.: 475,391

[22] Filed: Mar. 15, 1983

[30] Foreign Application Priority Data

Mar. 22, 1982 [IT] Italy ................................ 20307 A/82

[51] Int. Cl.$^4$ ............................................. C07C 69/76
[52] U.S. Cl. ...................................... 560/056; 562/466
[58] Field of Search ........................... 560/56; 562/466

[56] References Cited

FOREIGN PATENT DOCUMENTS 0035305 9/1981 European Pat. Off. .............. 560/56
2042543 1/1982 United Kingdom .................. 560/56

*Primary Examiner*—Paul J. Killos
*Attorney, Agent, or Firm*—Stevens, Davis, Miller & Mosher

[57] ABSTRACT

Process for preparing esters of 2-(6'-methoxy-2'-naphthyl)-propionic acids via rearrangement of ketals of 2-iodo-1-(6'-methoxy-2'-naphthyl)-propan-1-one in a protic medium.

3 Claims, No Drawings

PROCESS FOR PREPARING ESTERS OF 2'-(6'-METHOXY-2-NAPHTHYL)-PROPIONIC ACID

This invention relates to a new process for preparing esters of 2-(6'-methoxy-2'-naphthyl)-propionic acid via rearrangement of ketals of 2-iodo-1-(6'-methoxy-2'-naphthyl)-propan-1-one in a protic medium.

More particularly the process according to this invention may be represented by the following scheme:

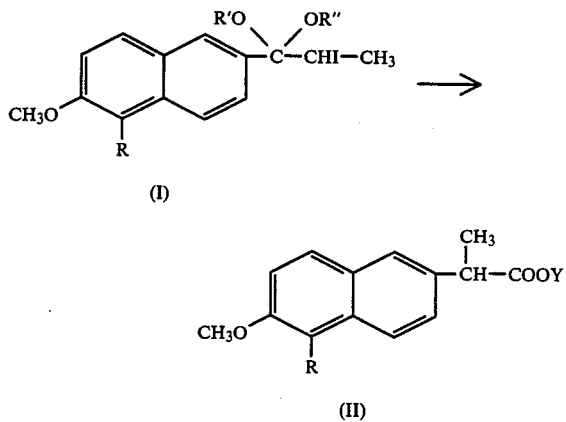

wherein
R is hydrogen or halogen;
R' and R" are an alkyl radical having from 1 to 6 carbon atoms, a benzyl radical or, together, are an alkylene radical having from 2 to 6 carbon atoms which, together with the

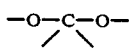

group to which they are linked, forms a heterocyclic ring;
Y is an alkyl radical having from 1 to 6 carbon atoms, an iodoalkyl radical having from 2 to 6 carbon atoms or a benzyl radical.

The esters of formula II may be hydrolized according to known methods to afford, when R is hydrogen, Naproxene.

When R is a halogen atom, the alkanoic acid obtained by hydrolysis of the ester of formula II is submitted to dehalogenation according to known methods to give Naproxene; examples of known methods are the catalytic hydrogenation or the reduction with Zn and formic or acetic acid. Alternatively the dehalogenation step may precede the hydrolysis.

The Applicants have already found (European Patent Application No. 35.305, filed on Feb. 24, 1981) that the same kind of rearrangement takes place when the ketals are placed in the presence of Lewis acids; it is a process which was making remarkably more easy the procedures known up to then for preparing Naproxene and it allows to obtain high yields.

Now it has been surprisingly found that 2-iodo-1-(6'-methoxy-2'-naphthyl)-propan-1-one rearranges to esters of 2-(6'-methoxy-2'-naphthyl)-propionic acid in the absence of a Lewis acid and in the presence of the same protic medium which catalyzes the ketalization step.

Protic media particularly useful to realize the object of this invention are alcohol/ortoformiate/protic acid or glycol/protic acid. As protic acid may be used sulfuric, methansulfonic, p-toluensulfonic, trichloroacetic, trifluoroacetic, oxalic acid etc.

The process according to this invention may be carried out at a temperature comprised between room temperature and the boiling temperature of the reaction mixture.

The reaction time ranges from few hours to 160 hours.

The meaning of Y in the formula II is correlated to the kind of the ketal and/or of the diluent.

If R' and R" are an alkyl or benzyl radical and the diluent is not nucleophilic then Y has the same meaning of R' and R".

When an alcohol is used as diluent, it may also take part to the esterification or transesterification step and subsequent formation of esters of formula II wherein Y is the alkyl radical of the alcohol used as diluent.

Furthermore, when the compound which is submitted to rearrangement is an alkylen-alpha-haloketal then Y in the ester of formula II may be, at least in part, an iodo-alkyl radical because the iodo atom of the iodo-ketone having formula I may replace the terminal hydroxy group of the glycol which is used as precursor of the ketal; meantime the other hydroxy group takes part to the formation of the ester.

The following example is intended only to illustrate but not to limit this invention.

EXAMPLE

In a 100 ml flask are placed 2-iodo-1-(6'-methoxy-2'-naphthyl)-propan-1-one (3.4 g.; 0.01 mols), methanol (5 ml.), trimethylorthoformiate (5 g.; 0.047 mols) and p-toluen-sulfonic acid (0.85 g.; 0.005 mols). The thus obtained mixture is heated at the reflux for 24 hrs. then the reaction mixture is cooled at room temperature, poured into water (200 ml.) and extracted with ethyl ether (3×100 ml.).

The ethereal solution is dried on anhydrous $Na_2SO_4$, filtered and evaporated to dryness. The residue is treated with methanol, 10 ml of 30% NaOH are added and the reaction mixture is heated at reflux for 2 hrs.

The reaction mixture is then cooled, poured into water (200 ml) and extracted with ethyl ether (3×100 ml). The aqueous solution is acidified at pH 1 with hydrochloric acid and extracted with ethyl ether (3×100 ml). The ethereal extracts are dried on anhydrous $Na_2SO_4$, filtered and evaporated to dryness. 1.1 g. (0.0048 mols) are thus obtained; yield 48% of 2-(6'-methoxy-2'-naphthyl)-propionic acid melting at 153°–155° C.

We claim:
1. Process for preparing an ester of a 2-(6'-methoxy-2'-naphthyl)-propionic acid of the formula

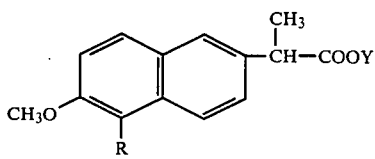

wherein
R is hydrogen or halogen; and

Y is an alkyl radical having from 1 to 6 carbon atoms, an iodoalkyl radical having from 2 to 6 carbon atoms, or a benzyl radical, by rearranging a compound having the formula

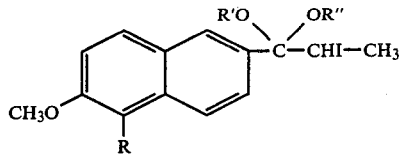

wherein

R has the above mentioned meaning; and

R' and R" are an alkyl radical having from 1 to 6 carbon atoms, a benzyl radical or, together, are an alkylene radical having from 2 to 6 carbon atoms which, together with the

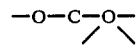

group to which they are linked, forms a heterocyclic ring, in the presence of a protic medium, and in the absence of a Lewis acid.

2. Process according to claim 1, characterized in that the protic medium consists of alcohol/orthoformiate/protic acid or of glycol/protic acid.

3. Process according to any one of the preceding claims 1 and 2, characterized in that the protic acid is selected from the group consisting sulphuric, methanesulfonic, p-toluen-sulfonic, trichloroacetic, trifluoroacetic, and oxalic acid.

* * * * *